United States Patent [19]

Kurimoto et al.

[11] Patent Number: 5,126,148

[45] Date of Patent: Jun. 30, 1992

[54] PROCESS TO PREPARE METASTASIS-INHIBITORY FACTOR

[75] Inventors: Masashi Kurimoto; Ryuichi Motoda; Kanso Iwaki, all of Okayama, Japan

[73] Assignee: Kaisha Hayashibara Seibutsu Kagaku Kenkyujo, Okayama, Japan

[21] Appl. No.: 526,143

[22] Filed: May 22, 1990

[30] Foreign Application Priority Data

May 22, 1989 [JP] Japan .................................. 1-128362

[51] Int. Cl.⁵ .................... A61K 35/12; A61K 35/28
[52] U.S. Cl. .................................................. 424/577
[58] Field of Search .......................................... 424/577

[56] References Cited

PUBLICATIONS

Gould Medical Dictionary, 4th ed., McGraw-Hill Book Company, 1979, p. 160.

*Primary Examiner*—Douglas W. Robinson
*Assistant Examiner*—Jean C. Witz
*Attorney, Agent, or Firm*—Browdy and Neimark

[57] ABSTRACT

Human hematopoietic cells produce metastasis-inhibitory factor (MIF). MIF exhibits a remarkable metastasis-inhibitory activity on viral diseases and immunopathies, as well as on malignant tumors. The MIF-producing human hematopoietic cells are easily proliferative by in vitro tissue culture and in vivo proliferation using a non-human warm-blooded animal. T cells exhibit a high MIF producibility. Mitogens augment the production of MIF when used as an MIF inducer.

9 Claims, No Drawings

PROCESS TO PREPARE METASTASIS-INHIBITORY FACTOR

BACKGROUND OF THE INVENTION

1. Field of the invention

The present invention relates to a process to prepare metastasis-inhibitory factor (abbreviated as "MIF" hereinafter), in particular, to a process to prepare MIF which comprises allowing an established human hematopoietic cell to produce MIF, and recovering the MIF.

2. Prior art

The expectation of life at birth in Japan is increasing year by year. According to *Nippon Tokei Nenkan (Japanese Statistical Yearbook)*, 37th edition, published by the Japan Statistical Association (1987), the expectation of life at birth in 1985 was 74.78 years for male and 80.48 years for female. The most predominant cause of death is malignant neoplasms or cancers which account for about 25% of the total death.

Treatment of cancers has been carried out predominantly with surgical operation, chemotherapy and irradiation. These therapies, however, can kill a major part of a growing cancer, but may disperse the remaining vial cancer cells in patient's body to accelerate its metastasis. This may result in a much more serious metastasizing cancer and shorten much more the remainder of patient's life.

If the metastasis of cancer is prevented, then the patients' pain is relieved and the remainder of their life may be remarkably prolonged. Thus, the development of any method which effectively suppresses the metastasis of cancers has been in great demand.

SUMMARY OF THE INVENTION

Accordingly, a main object of the present invention is to provide a process to prepare MIF which is easily feasible in industrial-scale.

We screened various metastasis-inhibitory substances which can be commercialized with ease, as well as studying their industrial-scale preparation.

As a result, we found that metastasis-inhibitory substances can be screened by checking them with RPMI 4788 cell (FERM BP-2429), an established human colon cancer cell, for their metastasis-inhibitory activity. Furthermore, we established a process to prepare MIF which comprises allowing an established human hematopoietic cell capable of producing MIF to produce MIF, and recovering the MIF. Thus, we accomplished the present invention.

DETAILED DESCRIPTION OF THE INVENTION

The wording "established human hematopoietic cell" includes those which are described, for example, in *Protein, Nucleic Acid and Enzyme*, Vol.20, No.6, pp.616-643 (1975), *Catalogue of the Japanese Cancer Research Resources Bank*, (1988), and *Catalogue of ATCC Cell Lines Hybridomas*, 6th edition (1988).

Established human hematopoietic cells which are grouped into T cell, B cell, non T.non B cell and myelomono-cytic cell are suitably chosen. For example, human T cells such as CCRF-CEM cell, HPB-MLT cell, MOLT-3 cell, MOLT-4 cell, P12/ICH cell and TALL-1 cell are superior in view of the commercialization of MIF because they exhibit a high MIF producibility.

The proliferation rate and MIF producibility of such a human cell are augmentable by introducing genes which encode MIF production into a much more readily subculturable established cell, for example, by means of cell fusion technique using polyethylene glycol or Sendai virus, or by conventional gene recombinant technique using DNA ligase, restriction enzyme (nuclease) and DNA polymerase.

The proliferation method for such a human cell is suitably chosen. Examples of such a method include both in vitro tissue culture method wherein a established human hematopoietic cell is inoculated and proliferated in a nutrient culture medium, and in vivo method wherein an established human hematopoietic cell is first implanted in the body of a non-human warm-blooded animal or inoculated in a diffusion chamber provided outside or inside the body of a non-human warm-blooded animal, then allowed to grow while receiving the nutrient body fluid from the body of the animal.

The in vitro method will be explained at first.

The in vitro method is feasible with any nutrient culture medium, as long as an established human hematopoietic cell is proliferative when inoculated therein; for example, RPMI 1640 medium and Eagle's minimal essential medium which can be supplemented with vitamins, minerals, carbohydrates, amino acids and sera from mammals, if necessary.

In the culture, monolayer culture and suspension culture are suitably chosen.

The temperature is set to about 20°-40° C., preferably, about 35°-38° C., while the inoculum is chosen such that a maximum cell growth is attained within an about 1 week after the inoculation, desirably, about $10^4$-$10^7$ in terms of the cell number/ml culture medium.

A culture medium with such an inoculum is incubated under these conditions for about 4-10 days while supplying sufficient nutrients thereto and washing or diluting the metabolites released in the culture medium by replacing it at intervals with fresh one The in vivo method will be explained hereinafter.

In this method, an established human hematopoietic cell is readily proliferative while utilizing the nutrient body fluid supplied from the body of a non-human warm-blooded animal by first implanting the human cell in the body of the animal, and, alternatively, placing the human cell in a diffusion chamber which can supply thereto the nutrient body fluid, then feeding the animal in usual manner. Thus, unlike the in vitro tissue culture method, the in vivo method yields a large amount of MIF even when expensive serum and nutrient culture medium are neglected or cut by a large margin.

More particularly, the method using a non-human warm-blooded animal facilitates the maintenance and control during the cell proliferation, as well as realizing a much more stabilized cell proliferation and augmented MIF production per cell, in particular, 2-10-fold or much higher than in the case of culturing in vitro.

The in vivo method is feasible with an non-human warm-blooded animal, as long as an established human hematopoietic cell is proliferative therewith; for example, fowls such as chicken and pigeon, and mammals such as dog, cat, monkey, goat, pig, cow, horse, rabbit, guinea pig, rat, hamster, mouse and nude mouse.

Since implantation of such a human cell has a fear of causing undesirable immunoreactions, it is desirable to use a non-human warm-blooded animal in its possible youngest stage such as egg, embryo or fetus, and newborn and infant animals, in order to suppress such an immunoreaction as far as possible.

These animals can be pretreated, for example, with x-ray or γ-ray irradiation, about 200–600 rem, or with injection of antiserum or immunosuppressant to weaken the possible immunoreaction, prior to the implantation.

Particularly, since nude mouse exhibits a less immunoreaction even when in its adulthood, any established human hematopoietic cell is implantable and readily proliferative without such a pretreatment. These are because the use of nude mouse is very favorable.

One can obtain a stabilized proliferation of an established human hematopoietic cell and/or an increased amount of MIF by successively implanting the human cell in different non-human warm-blooded animals; for example, by first implanting and proliferating the human cell in a hamster, then transplanting the proliferated human cells in a nude mouse.

In this case, animals in the sam class and phylum are usable, as well as those in the same species and genus. Established human hematopoietic cells are implantable in any site of the animal, as long as they are proliferative in the site when implanted; for example, allantoically, intravenously, intraperitoneally and subcutaneously.

In addition to direct implantation in the body of an animal, either of the above described human cells is proliferative by embedding in the body of an animal, for example, intraperitoneally, conventional diffusion chamber with a macroporous filter of various shapes and sizes, such as membrane filter, ultra filter and hollow fiber, pore size of about $10^{-7}$–$10^{-5}$ m, which can stop the penetration of animal cells but supply the nutrient body fluid to the human cell.

If necessary, such a diffusion chamber can be connected and placed, for example, on an animal such that both nutritive solution in the diffusion chamber and body fluid can circulate through the diffusion chamber. Thus, one can observe proliferating human hematopoietic cells through a chamber wall, and/or the diffusion chamber per se is replaceable with a fresh one both to continue the proliferation over the period of the life span of the animal without sacrificing it and to augment much more the cell production per animal.

Since due to the absence of direct contact of a human cell with an animal cell, such a diffusion chamber elicits a much less undesirable immunoreaction, any non-human warm-blooded animal can be readily used without pretreatment to reduce such a immunoreaction, and the proliferated viable human cell can be easily recovered from the diffusion chamber.

Feeding of the animal is carried out in usual manner, and no special care is required even after the implantation.

The period required to obtain a prescribed proliferation is usually about 1–10 weeks.

The number of the human cells thus obtained is about $10^7$–$10^{12}$ cells or more per animal.

More particularly, the number of human hematopoietic cells proliferated by the method using a non-human warm-blooded animal reaches up to about $10^2$–$10^7$-fold or more, which is about $10$–$10^6$-fold or higher than that obtained by inoculating and proliferating in vitro a human hematopoietic cell in a nutrient culture medium. This is very favorable in the preparation of MIF.

The method to prepare MIF with the human hematopoietic cell thus obtained should not be restricted to special one. The human cell is exposed to an MIF inducer in the animal wherein the human cell has grown.

For example, a human hematopoietic cell, proliferated in ascite in suspension, or a tumor cell, formed, for example, subcutaneously, is exposed in vivo directly to an MIF inducer to induce MIF production, and the resultant MIF is recovered from the ascite, serum and/or tumor, and then purified.

Alternatively, the proliferated human cell is recovered from the animal and then exposed in vitro to an MIF inducer. For example, a human cell which is recovered from an ascite suspension, or obtained by extracting and disaggregating tumor mass(es), formed, for example, subcutaneously, is suspended in a nutrient culture medium, kept at about 20°–40° C., to give a cell density of about $10^5$–$10^8$ cells/ml, and exposed to an MIF inducer to induce MIF production. Thereafter, the resultant MIF is recovered and purified.

When a human hematopoietic cell is proliferated in a diffusion chamber, the proliferated human cell is exposed in the diffusion chamber to an MIF inducer to induce MIF production, and, alternatively, recovered from the diffusion chamber prior to the induction.

The MIF production per animal can be further augmented by employing a method wherein a proliferated human cell is exposed to an MIF inducer in the body of an animal, recovered from certain site(s) of the animal or its whole body, and exposed in vitro to an MIF inducer to induce MIF production; another procedure wherein a human cell is repeatedly exposed to an MIF inducer; and/or one another procedure wherein a diffusion chamber which is embedded in or connected to the body of an animal is replaced at intervals with fresh one.

As to MIF inducers, for example, mitogens such as phytohemagglutinin, concanavalin A, pokeweed mitogen, lipopolysaccharide, lipid A, endotoxin, polysaccharide, bacteria, virus, nucleic acid and polynucleotide are suitable.

Such an MIF inducer is usually used at a concentration from about 0.001 µg/ml to 10 mg/ml. Two or more MIF inducers are freely usable in combination in order to increase MIF and to induce a simultaneous production of other lymphokine(s).

The MIF thus obtained can be easily recovered by the purification and separation using conventional procedure, for example, salting-out, dialysis, filtration, centrifugation, concentration and lyophilization. When a much higher purification is needed, for example, adsorption and desorption with ion exchange, gel filtration, affinity chromatography, isoelectric point fractionation, high-performance liquid chromatography, column chromatography, and electrophoresis are used in combination. Particularly, one can recover MIF in its possible purest form by the chromatography using an monoclonal antibody.

The MIF obtained in this way is favorably usable in preventive and remedy for MIF-susceptive diseases.

The wording "MIF-susceptive diseases" means those which can be prevented and/or treated with MIF; in particular, viral diseases, for example, epidemic conjunctivitis, herpetic keratitis, influenza, rubella, serum hepatitis and acquired immune deficiency syndrome (AIDS); and non-viral diseases, for example, malignant tumors including colon cancer, lung cancer, liver cancer and osteosarcoma, and immunopathies such as atopic allergy, myastheniagravis, collagen disease, malignant anemia, articular rheumatism and systemic lupus erythematodus.

The shape and form of such a preventive and remedy are freely chosen to meet their final use; for example, liquid agents such as nebula, collyrium, collutory and injection, paste agents such as ointment and cataplasm, and solid agents such as powder, granule, capsule and tablet.

These preventive and remedy are generally incorporated with about 1–10,000,000 units/g of MIF. If necessary, they can be incorporated with one or more lymphokines, and/or natural or synthetic chemotherapeutics, for example, interferon-α, interferon-β, interferon-γ, tumor necrosis factor, lymphotoxin, interleukin 1, interleukin 2 and B-cell differentiating factor, in order to augment their prophylactic and therapeutic activities.

Of course, one or more adjuvants, augmentors and stabilizers can be used in combination.

The preventive and remedy thus obtained are favorably usable, for example, in antiviral agents, antitumor agents, augmentors for antitumor chemotherapeutics, preventives for the recurrent of malignant tumors, immunoregulators, and remedies for immunopathies, as well as in suppressants for the metastasis of cancers.

The activity of MIF was determined in accordance with the method reported in Y. Naomoto et al., *Journal of Cancer Research Clinical Oncology*, Vol. 113, pp.544–549 (1987) with a slight modification, wherein a lung metastasis is induced with RPMI 4788 cell (FERM BP-2429), an established human colon cancer cell, in nude mice which are then administered with a liquid sample containing MIF to determine its metastasis-inhibitory activity.

More particularly, BALB/c nude mice are inoculated via the tail vein with $2 \times 10^6$ viable RPMI 4788 cells in 0.2 ml saline. From the next day, the nude mice are injected via the tail vein with 0.1 ml aliquot of an MIF-containing liquid sample every day for 10 days. On the 21st day, the nude mice are sacrificed, and the nodules on their lung surface are stained and counted for metastases of RPMI 4788 cell. Saline is used as the control, and 8 nude mice are used for each liquid sample. One thousand units of MIF is defined as the amount of MIF that halves the number of nodules, provided that the control forms 100 or more nodules under these conditions. Interferon-α, interferon-β, interferon-γ, tumor necrosis factor-α, tumor necrosis factor-β, interleukin 1 and interleukin 2 are removed from the liquid sample prior to its use if it contains either of them.

The hemagglutination titers were assayed in accordance with the method reported by S. E. Salk, *The Journal of Immunology*, Vol.49, pp.87–98 (1944) with a slight modification.

The following Experiments will explain the present invention in detail.

Experiment

Comparison of established human hematopoietic cells for their MIF producibility

Experiment 1

MIF production by the cell proliferated in vitro

One variety of established human cells was inoculated in RPMI 1640 medium (pH 7.2) supplemented with 20 v/v % fetal calf serum, cultured at 37° C. in usual manner, washed with serum-free RPMI 1640 medium (pH 7.2), and suspended in a fresh preparation of the same culture medium to give a cell density of about $5 \times 10^6$/ml.

The resultant cell suspension was added with 10 μg/ml bacillus Calmette-Guerin incubated at 37° C. for 1 day, further added with 1 μg/ml lipopolysaccharide, incubated at 37° C. for an additional 1 day to induce MIF production, and centrifuged. The supernatant was concentrated by 50-folds with a membrane having lower molecular weight limit of 6,000, and then determined for MIF activity per ml.

The results were as shown in Table I.

As obvious from the results in Table I, established human hematopoietic cells have an MIF producibility. Particularly, we found that T cells were higher in MIF producibility. HPB-MLT cell (FERM BP-2430), which is remarkably high in MIF producibility, is favorably usable in the invention.

TABLE I

| T cell | | | |
|---|---|---|---|
| CCRF-CEM | HPB-MLT | MOLT-3 | TALL-1 |
| 900 | 4,600 | 1,300 | 700 |

| B cell | | | |
|---|---|---|---|
| NALM-1 | KLM-2 | Namalwa | BALL-1 |
| less then 20 | less than 20 | less than 20 | 50 |

| non T.non B cell | | | |
|---|---|---|---|
| KM-3 | NALL-1 | NOPN-K | BV-173 |
| 40 | less than 20 | less than 20 | less than 20 |

| Myelomonocytic cell | | | |
|---|---|---|---|
| HL-60 | THP-1 | U-937 | KG-1 |
| less than 20 | less than 20 | 60 | 40 |

Note: The values represent MIF activities (units).

Experiment 2

MIF production by the cells proliferated in vivo

Newborn hamsters were injected with an antiserum prepared from rabbit by conventional method to weaken their immunoreaction, subcutaneously implanted with one variety of established human hematopoietic cells, and fed for 3 weeks in usual manner. The tumor masses, formed subcutaneously in the hamsters, were extracted, minced, disaggregated by suspending them in a saline containing trypsin, and recovered.

Thereafter, each cell was prepared into suspension similarly as in Experiment 1, and then determined for its MIF activity. The results were as shown in Table II.

TABLE II

| T cell | | | |
|---|---|---|---|
| CCRF-CEM | HPB-MLT | MOLT-3 | TALL-1 |
| 2,100 | 17,500 | 5,200 | 21,000 |

| B cell | non T.non B cell | Myelomonocytic cell | |
|---|---|---|---|
| BALL-1 | KM-3 | U-937 | KG-1 |
| 150 | 70 | 150 | 100 |

Note: The values represent MIF activities (units).

Experiment 3

Partial purification of MIF

HPB-MLT cells, proliferated by the method in Experiment 2, were allowed to produce MIF and centrifuged by the method in Experiment 1 with a slight modification. The supernatant was then concentrated by 50-folds with a membrane, lower molecular weight limit of 6,000, and chromatofocused on "PBE-94", a gel product of Pharmacia LKB Biotechnology, Upsala, Sweden. The MIF-rich fractions (pH 5–7) were recovered and subjected to a gel filtration chromatography using "Sephacryl S-200", a gel product of Pharmacia LKB Biotechnology, Upsala, Sweden, and newly-formed MIF-rich fractions, molecular weight of 10,000–450,000, were recovered and concentrated to obtain a partially purified liquid sample containing about 2,800,000 units/ml of MIF in the activity recovery yield of about 60%.

The product suppresses, in addition to the lung metastasis of RPMI 4788 cell, a human colon cancer cell, the liver metastasis of Lovo cell (ATCC CCL 229), a human colon cancer cell.

The product is favorably usable in the treatment of cancer patients alone or in combination with other lymphokine, chemotherapeutic, surgical operation and/or irradiation.

Several embodiments of the invention will be described hereinafter.

EXAMPLE 1

RAMOS cell (ATCC CRL 1596) was inoculated in RPMI 1640 medium (pH 7.2), supplemented with 10 v/v % fetal calf serum, to give a cell density of $5 \times 10^5$ cells/ml Thereafter, the cell was cultured at 37° C. while refreshing at intervals the culture medium, washed with a fresh preparation of the same culture medium, and suspended in the same culture medium to give a cell density of $2 \times 10^6$ cells/ml. The suspension was added with BCG and lipopolysaccharide in respective amount of about 10 μg/ml, and incubated at 37° C. for 2 days to induce MIF production. Centrifugation of the resultant culture yielded a supernatant which contained about 60 units/ml MIF.

EXAMPLE 2

Newborn hamsters were injected with an antiserum prepared from rabbit by conventional method to weaken their immunoreaction, subcutaneously implanted with HPB-MLT cell (FERM BP-2430), and fed for 5 weeks in usual manner. The tumor masses, formed subcutaneously in the hamsters, about 20 g each, were extracted, disaggregated by suspending them in a saline containing collagenase, and recovered.

The obtained cell was washed with Eagle's minimal essential medium, diluted in a fresh preparation of the same medium, kept at 37° C., to give a cell density of about $2 \times 10^6$ cells/ml, added with 200 μg/ml phytohemagglutinin and 5 μg/ml lipid A, and incubated at 37° C. for 2 days to induce MIF production. Centrifugation of the resultant culture yielded a supernatant which contained about 9,400 units/ml MIF. Thus, about 16,500,000 units of MIF was obtained per hamster.

EXAMPLE 3

Newborn rats were intravenously implanted with MOLT-3 cell (ATCC CRL 1552), and fed for 4 weeks in usual manner.

The tumor masses, formed subcutaneously in the rats, about 20 g each, were extracted and disaggregated similarly as in Example 2 to obtain a cell suspension which was then added with about 100 hemagglutination titers/ml Sendai virus and about 5 μg/ml lipopolysaccharide, and incubated at 37° C. for 2 days to induce MIF production.

The resultant culture was centrifuged, ultracentrifuged, and membrane-filtered for the removal of the virus to obtain about 4,200 units MIF per ml filtrate. Thus, about 6,900,000 units of MIF was obtained per rat.

EXAMPLE 4

TALL-1 cell (JCRB 0086) was suspended with saline in about 10 ml plastic cylindrical diffusion chambers having a membrane filter, pore size of about 0.5 μ, which were then intraperitoneally embedded in adult rats.

The rats were then fed in usual manner for 4 weeks, and the diffusion chambers were removed.

The cells were recovered from the diffusion chambers, and treated similarly as in Example 1 to induce MIF production. Centrifugation of the resultant culture yielded a supernatant which contained about 1,600 units/ml MIF. Thus, about 1,800,000 units of MIF was obtained per rat.

EXAMPLE 5

U-937 cell (ATCC CRL 1593) was implanted in embryonated eggs which had been kept at 37° C. for 5 days, and incubated at 37° C. for 1 week. The eggs were then cracked, and the proliferated cells were recovered. Thereafter, the cells were treated similarly as in Example 2 to induce MIF production. Centrifugation of the resultant culture yielded a supernatant which contained about 120 units/ml MIF. Thus, about 9,000 units of MIF was obtained per 10 embryonated eggs.

As described above, the present invention is to establish a process to prepare MIF using human hematopoietic cells.

Besides suppressing the metastasis of cancers to relieve patients' pain and prolong the remainder of their life, MIF is useful in preventive and remedy for MIF-susceptive diseases, for example, viral diseases, malignant tumors and immunopathies. Thus, MIF is very significant in pharmaceutical industry.

We claim:

1. A process for the production of concentrated metastasis-inhibitory factor (MIF), comprising:
    culturing an established human hematopoietic cell line capable of producing MIF;
    exposing the cell line to a nitrogen capable of inducing MIF;
    recovering the supernatant;
    subjecting the supernatant to chromatofocusing and covering the fractions at pH 5–7;
    subjecting the obtained fraction to gel filtration chromatography and recovering the fraction with a molecular weight of 10,000–450,000; and
    removing any interferon-α, interferon-β, interferon-γ, tumor necrosis factor-α, tumor necrosis factor-β, interleukin 1 and interluekin 2,
    whereby a fraction is obtained which is rich in MIF which exhibits metastasis-inhibitory activity when assayed with an established human colon cancer cell, RPMI 4789 (FERM BP-2429).

2. A process in accordance with claim 1, wherein said MIF-inducer is selected from the group consisting of phytohemaggiutinim, concanavalin A, pokeweed mitogen, bacillus Calmette-Guevin, Sendal virus lipopolysaccharide, lipid A and endotoxin.

3. The process of claim 1, wherein said human hematopoietic cell is obtainable by:
    implanting an established human hematopoietic cell in the body of a non-human warm-blooded animal; and feeding the animal while allowing the human hematopoietic cell to receive the nutrient body fluid from the body of the animal for its proliferation.

4. The process of claim 3, wherein said non-human warm-blooded animal is a fowl or a mammal.

5. The process of claim 1, wherein said human hematopoietic cell is obtainable by:

inoculating an established human hematopoietic cell in a diffusion chamber provided inside or outside of the body of a non-human warm-blooded animal; and feeding the animal while allowing the human hematopoietic cell to receive the nutrient body fluid from the body of the animal for its proliferation.

6. The process of claim 5, wherein said non-human warm-blooded animal is a fowl or a mammal.

7. The process of claim 1, wherein said human hematopoietic cell is a T cell.

8. The process of claim 1, wherein said established human hematopoietic cell is a member selected from the group consisting of RAMOS cell (ATCC CRL 1596), HPB-MLT cell (FERM BP-2430), MOLT-3 cell (ATCC CRL 1552), TALL-1 cell (JCRB 0086), and U-937 cell (ATCC CRL 1593).

9. MIF produced by the process of claim 1.

* * * * *